United States Patent [19]

Goldkamp et al.

[11] 4,025,551

[45] May 24, 1977

[54] 3-AMINO-N-SUBSTITUTED SUCCINAMIC ACIDS

[75] Inventors: Arthur H. Goldkamp, Bellevue, Wash.; Robert H. Mazur, Deerfield; James M. Schlatter, Glenview, all of Ill.

[73] Assignee: G. D. Searle & Co., Chicago, Ill.

[22] Filed: Dec. 22, 1975

[21] Appl. No.: 642,890

Related U.S. Application Data

[63] Continuation-in-part of Ser. No. 442,431, Feb. 14, 1974, which is a continuation-in-part of Ser. No. 56,753, July 20, 1970, Pat. No. 3,803,233, which is a continuation-in-part of Ser. No. 704,229, Feb. 9, 1968, abandoned.

[52] U.S. Cl. .................. 260/518 R; 260/247.2 A; 260/295 AM; 260/295 CA; 260/326.14 R; 260/332.2 A; 260/340.5; 260/347.3; 260/347.4; 260/468 E; 260/471 C; 260/482 C; 260/501.1; 260/518 A; 260/519; 260/534 R; 424/319

[51] Int. Cl.² ............. C07C 101/72; C07C 101/10; C07C 101/16; C07C 101/02

[58] Field of Search ....... 260/518 R, 520 C, 518 A, 260/519

[56] References Cited

UNITED STATES PATENTS

| | | | |
|---|---|---|---|
| 3,206,439 | 9/1965 | Detoro et al. | 260/518 R |
| 3,214,377 | 10/1965 | Hotten | 260/518 R |
| 3,222,395 | 12/1965 | Schultz et al. | 260/518 R |
| 3,313,847 | 4/1967 | Tate et al. | 260/518 R |
| 3,488,737 | 1/1970 | Gordon | 260/518 R |
| 3,576,854 | 4/1971 | Felder et al. | 260/518 R |
| 3,803,223 | 4/1974 | Mazur et al. | 260/534 R |
| 3,888,899 | 6/1975 | Greve et al. | 260/518 R |

OTHER PUBLICATIONS

Goldkamp et al., U.S. Pub. Pat. Appl. No. B442,431, Mar. 23, 1976.

*Primary Examiner*—Norman Morgenstern
*Attorney, Agent, or Firm*—John J. McDonnell

[57] ABSTRACT

3-Amino-N-substituted succinamic acids, prepared by coupling of a protected L-aspartic acid derivative with the appropriate amine followed by cleavage of the protecting groups, are potent sweetening agents and also exhibit pharmacological, e.g. anti-inflammatory, properties.

13 Claims, No Drawings

3-AMINO-N-SUBSTITUTED SUCCINAMIC ACIDS

This application is a continuation-in-part of our copending application Ser. No. 442,431, filed Feb. 14, 1974, which is a continuation-in-part of our copending application Ser. No. 56,753, filed July 20, 1970, now U.S. Pat. No. 3,803,233 which is a continuation-in-part of our copending application Ser. No. 704,229, filed Feb. 9, 1968, and now abandoned.

The present invention relates to novel 3amino-N-substituted succinamic acids of the following structural formula

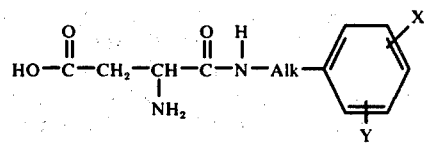 (I)

wherein Alk is an alkylene radical containing 2 to 6 carbon atoms and X and Y are selected from the group consisting of hydrogen, halogen, hydroxy and lower alkoxy, with the proviso that when Alk contains 2 carbon atoms, then the phenyl ring must be substituted by at least one halogen, hydroxy or lower alkoxy radical, and relates also to the novel intermediates used in the manufacture of the latter compounds.

The lower alkyl radicals containing 1 to 6 carbon atoms encompassed in the foregoing structural formula are typified by methyl, ethyl, propyl, butyl, pentyl, hexyl, and the branched-chain radicals isomeric therewith.

Typical of the alkylene radicals containing 2 to 6 carbon atoms denoted by Alk are ethylene, trimethylene, tetramethylene, pentamethylene and the corresponding branched-chain isomers.

The halogen substituents encompassed in that formula are fluoro, chloro, bromo and iodo.

Representative of the lower alkoxy radicals denoted above are methoxy, ethoxy, propoxy, butoxy, pentyloxy, hexyloxy, and the corresponding branched-chain isomers.

Particularly preferred compounds of the present invention are those of the formula

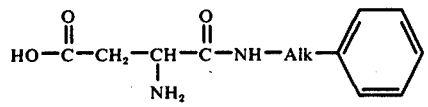

wherein Alk is an alkylene radical containing 3 to 6 carbon atoms.

The novel compounds of the present invention are conveniently obtained by a two-step process which comprises the coupling of a suitable L-aspartic acid derivative, wherein protecting groups are attached to the amino and β-carboxy groups, with the appropriate amine, followed by removal of the protecting groups, suitably by catalytic hydrogenolysis. Examples of suitable starting materials are β-benzyl N-benzyloxycarbonyl-L-aspartate and active esters thereof such as N-benzyloxycarbonyl-L-aspartic acid α-p-nitrophenyl, β-benzyl diester. When the starting material contains the free α-carboxy group, the reaction is carried out in the presence of an alkyl chloroformate and a suitable organic base. β-Benzyl-N-benzyloxycarbonyl-L-aspartate is thus allowed to react, for example, with DL-1-methyl-4'-fluorophenethylamine in the presence of ethyl chloroformate and N-methylmorpholine to afford benzyl 3-benzyloxycarbonylamino-N-DL-1'-methyl-4''-fluorophenethyl-L-succinamate. The use of an active ester is exemplified by the reaction of N-benzyloxycarbonyl-L-aspartic acid p-nitrophenyl, β-benzyl diester with DL-1-methyl-4'-hydroxyphenethylamine, thus affording 3-benzyloxycarbonylamino-N-DL-1-methyl-4'-hydroxyphenethyl-L-succinamate.

Removal of the protecting groups of the aforementioned novel intermediates is most conveniently achieved by catalytic hydrogenolysis, preferably by use of a palladium black catalyst. When benzyl 3-benzyloxycarbonylamino-N-L-1'-methylphenethyl-L-succinamate, for example, is shaken in methanol with hydrogen in the presence of palladium black at room temperature and a pressure of about 4 atmospheres, 3-amino-N-L-1'-methylphenethyl-L-succinamic acid is produced.

An alternate process for production of the instant compounds utilizes the N-carboxy anhydride of L-aspartic acid as the starting material. That substance is prepared from L-aspartic acid by reaction with phosgene and dioxane according to the general procedure described by Farthing, A. C., *J. Chem. Soc.*, 1950, 3213. The N-carboxy anhydride is coupled with the appropriate amine in aqueous medium at a pH of about 10 according to the general procedure described by Hirschmann et al., *J. Org. Chem.* 32, 3415 (1967). This alternate procedure offers the advantage of obviating the steps involving the addition and subsequent removal of protecting groups. A specific illustration is the reaction of L-aspartic acid N-carboxy anhydride with DL-1-methyl-4'-fluorophenethylamine to yield 3-amino-N-DL-1'-methyl-4''-fluorophenethyl-L-succinamic acid.

The 3-amino-N-substituted succinamic acids of the present invention are surprisingly and unexpectedly characterized by a sweet taste, thus are useful for the purpose of imparting that taste to food products. These compounds can thus be added to food products such as fruits, vegetables, juices, meat products such as ham or bacon, sweetened milk products, egg products, salad dressings, ice creams and sherbets, gelatins, icings, syrups, cake mixes, chewing gums and beverages such as carbonated soft drinks and wines.

The preparation of a typical sweetened orange soda is described as follows:

A stock supply of bottler's syrup is prepared by mixing 5.5 ml. of a 50% aqueous citric acid solution with 150 ml. of water, dissolving 2 g. of 3-amino-N-L-1'-methylphenethyl-L-succinamic acid in that solution, adding successively 7.02 ml. of the orange flavor base manufactured by A. E. Illes, Dallas, Tex., labeled FO-78, and 2.7 g. of sodium benzoate and diluting that mixture to 200 ml. with water. One ounce samples of that bottler's syrup are transferred to 6 ounce bottles and 110 ml. of cold tap water is added to each bottle. To each bottle 42 ml. of cold charged bottling water (5 volumes carbon dioxide) is then added to achieve carbonation. Each bottle is capped and the contents mixed.

The latter preparation possesses a sweetness comparable to that containing a quantity of sucrose 50 times that of the named succinamic acid derivative.

The instant sweetening agents are stable substances and can be utilized in a variety of physical forms, e.g. as powders, tablets, syrups, etc. Liquid or solid carriers such as water, glycerol, starch, sorbitol, salt, citric acid and other suitable non-toxic substances can be used also. These agents are particularly useful as sugar substitutes for diabetics. They are, moreover, advantageous over synthetic sweetening agents such as saccharin and cyclamate by virtue of the absence of an unpleasant after-taste.

It has been determined that the sweetening property of the instant compounds is highly dependent upon the stereochemistry of the molecule. The corresponding D-aspartic acid and D-amine derivatives are thus totally lacking in this sweetening property.

The 3-amino-N-substituted succinamic acids of this invention are, furthermore, useful as pharmacological agents, as is evidenced, for example, by their anti-inflammatory properties. For that purpose, these substances can be administered in conventional pharmaceutical forms and by conventional routes. Solid forms such as pills, powders, capsules, tablets and the like and liquid forms such as syrups, emulsions, elixirs, suspensions and the like are suitable for oral administration, while aqueous solutions or suspsensions or solutions in pharmacologically acceptable oil or oil-water emulsions are suitable for parenteral administration. Suitable excipients can also be added.

The anti-inflammatory activity of the compounds of this invention is determined by the following assay:

Each of a group of 10 intact male rats weighing 100-130 grams is injected, under the plantar surface of each hind foot, with 0.1 ml. of a 1% solution of carrageenin (Type 402, Marine Colloids, Inc.). The test compound, dissolved or suspended in saline, corn oil or propylene glycol, is administered subcutaneously one hour prior to the carrageenin injection. Another such group serving as controls is treated in the identical manner save for omission of the test compound. The edema resulting from carrageenin injection is determined by measuring the circumference of the hind feet, in arbitrary units, 5 hours after the carrageenin injection and subtracting the average swelling of the group treated with the test compound from the average swelling of the control group. Compounds are rated active if they produce a significant decrease (P<0.05) in the swelling observed in control animals.

The invention will appear more fully from the examples which follow. It will be apparent to those skilled in the art that many modifications, both of materials and methods, may be practiced without departing from the purpose and intent of this disclosure. In these examples temperatures are given in degrees Centigrade (° C.) and quantities of materials in parts by weight unless otherwise noted.

EXAMPLE 1

To a solution of 4.53 parts of DL-2-amino-1-phenylpropanol in 22.5 parts of dimethylformamide is added 15.06 parts of N-benzyloxycarbonyl-L-aspartic acid α-p-nitrophenyl, β-benzyl diester and the resulting reaction mixture is stirred for a few minutes until homogeneous, then is allowed to stand at room temperature for about 16 hours. At the end of that reaction period the mixture is diluted with ethyl acetate, then washed successively with dilute hydrochloric acid, water, dilute aqueous potassium bicarbonate and dilute aqueous sodium sulfate, and dried over anhydrous sodium sulfate, then stripped of solvent by distillation under reduced pressure. The residue thus obtained is triturated with cyclohexane to afford the crude product, melting at about 70°-80° C. and that crude material is further purified by recrystallization from aqueous isopropyl alcohol to afford benzyl 3-benzyloxycarbonylamino-N-DL-1'-methyl-2'-hydroxyphenethyl-L-succinamate, melting at about 72°-84° C. and displaying an optical rotation, in methanol, of −9°.

EXAMPLE 2

A solution containing 17.85 parts of β-benzyl N-benzyloxycarbonyl-L-aspartate, 5.9 parts by volume of N-methylmorpholine and 76.5 parts of anhydrous tetrahydrofuran is cooled to approximately −20° C. and 7 parts by volume of isobutyl chloroformate is added dropwise with vigorous stirring while the temperature is maintained between −10° and −15° C. Stirring at that temperature is continued for about 5 minutes, at the end of which time the mixture is cooled to approximately −30° C. At that point, 8.25 parts by volume of DL-1,4-dimethylpentylamine is added dropwise with vigorous stirring while the temperature is maintained between −10° C and −15° C. After that addition is complete, the reaction mixture is kept at approximately 5° C. for about 16 hours. The reaction mixture is then diluted with ethyl acetate, washed successively with dilute hydrochloric acid, dilute aqueous sodium sulfate and dilute aqueous potassium bicarbonate, then dried over anhydrous sodium sulfate and stripped of solvent under reduced pressure. The resulting residual crude product is purified by trituration with hexane to afford benzyl 3-benzyloxycarbonylamino-N-DL-1',4'-dimethylpentyl-L-succinamate, melting at about 90°-103° C. This compound exhibits an optical rotation, in methanol, of −7°.

EXAMPLE 3

The substitution of 4.53 parts of DL-1-methyl-4'-hydroxyphenethylamine in the procedure of Example 1 affords benzyl 3-benzyloxycarbonylamino-N-DL-1'-methyl-4''-hydroxyphenethyl-L-succinamate, which, after recrystallization from cyclohexane, melts at about 106°-117° C. and exhibits an optical rotation, in methanol, of −9.5°. This compound is represented by the following structural formula.

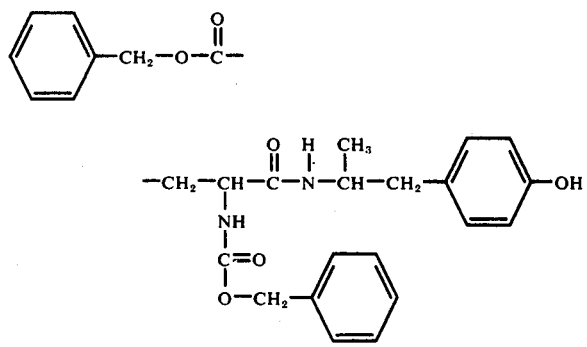

EXAMPLE 4

The reaction of 15.18 parts of DL-1-methyl-4'-fluorophenethylamine, 28.6 parts of β-benzyl N-benzyloxycarbonyl-L-aspartate, 8.72 parts of ethyl chloroformate and 19.3 parts of N-methylmorpholine according to the procedure of Example 2 results in benzyl 3-benzyloxycarbonylamino-N-DL-1'-methyl-4''-fluorophenethyl-L-succinamate, melting at about 82.5°–87° C., and represented by the following structural formula.

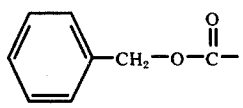

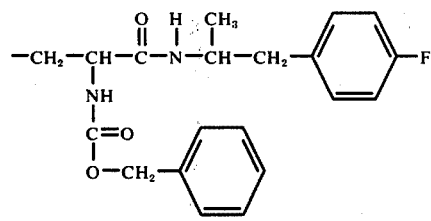

EXAMPLE 5

The reaction of 21.5 parts of N-benzyloxycarbonyl-L-aspartic acid β-benzyl ester, 14.4 parts of DL-1-methyl-3′,-4′-dichlorophenethylamine, 6.54 parts of ethyl chloroformate and 14.5 parts by volume of N-methylmorpholine according to the procedure of Example 2 results in benzyl 3-benzyloxycarbonylamino-N-DL-1′-methyl-3″,4″-dichlorophenethyl-L-succinamate, melting at about 92°–107° C.

EXAMPLE 6

When 28.6 parts of β-benzyl N-benzyloxycarbonyl-L-aspartate, 16.5 parts of DL-1-methyl-4′-chlorophenethylamine, 8.72 parts of ethyl chloroformate and 19.3 parts by volume of N-methylmorpholine are allowed to react according to the procedure of Example 2, there is produced benzyl 3-benzyloxycarbonylamino-N-DL-1′-methyl-4″-chlorophenethyl-L-succinamate melting at about 95°–106° C.

EXAMPLE 7

The reaction of 3.11 parts of D-1-methylphenethylamine with 10.05 parts of N-benzyloxycarbonyl-L-aspartic acid α-p-nitrophenyl, β-benzyl diester according to the procedure of Example 1 affords benzyl 3-benzyloxycarbonylamino-N-D-1′-methylphenethyl-L-succinamate, which, after recrystallization from isopropyl acetate, melts at about 108°–109.5° C. and exhibits an optical rotation, in methanol, of +3.5°.

EXAMPLE 8

When 3.11 parts of L-1-methylphenethylamine is allowed to react with 10.05 parts of N-benzyloxycarbonyl-L-aspartic acid α-p-nitrophenyl, β-benzyl diester according to the procedure of Example 1, there is produced benzyl 3-benzyloxycarbonylamino-N-L-1′-methylphenethyl-L-succinamate, which, after recrystallization from isopropyl acetate, melts at about 118°–120.5° C. and displays an optical rotation, in methanol, of −23.5°.

EXAMPLE 9

The reaction of 6.16 parts of DL-1- ethylphenethylamine with 19.05 parts of N-benzyloxycarbonyl-L-aspartic acid α-p-nitrophenyl, β-benzyl diester according to the procedure of Example 1 results in benzyl 3-benzyloxycarbonylamino-N-DL-1′-ethylphenethyl-L-succinamate which, after recrystallization from isopropyl acetate-cyclohexane, melts at about 105°–115° C. and exhibits an optical rotation, in methanol, of −11°.

EXAMPLE 10

When 6.86 parts of 4-hydroxyphenethylamine and 20.1 parts of N-benzyloxycarbonyl-L-aspartic acid α-p-nitrophenyl, β-benzyl diester are allowed to react according to the procedure of Example 1, there is produced benzyl 3-benzyloxycarbonylamino-N-4′-hydroxyphenethyl-L-succinamate, which, after recrystallization from isopropyl acetate-cyclohexane, melts at about 148°–149.5° C. and exhibits an optical rotation, in methanol, of −12°.

EXAMPLE 11

When 9.33 parts of DL-2-methylphenethylamine is allowed to react with 30.15 parts of N-benzyloxycarbonyl-L-aspartic acid α-p-nitrophenyl, β-benzyl diester by the procedure of Example 1, there is produced benzyl 3-benzyloxycarbonylamino-N-DL-2′-methylphenethyl-L-succinamate, which, after recrystallization from isopropyl acetate, melts at about 72°–81° C. and exhibits an optical rotation, in methanol, of −15.5°.

EXAMPLE 12

When 8.32 parts of 4-methoxyphenethylamine is allowed to react with 23.9 parts of N-benzyloxycarbonyl-L-aspartic acid α-p-nitrophenyl β-benzyl diester according to the procedure of Example 1, there is produced benzyl 3-benzyloxycarbonylamino-N-4′-methoxyphenethyl-L-succinamate, which after recrystallization from isopropyl acetate, melts at about 135.5°–136.5° C.

EXAMPLE 13

The reaction of 8.2 parts of DL-1-methyl-3-phenyl-n-propylamine with 23.9 parts of N-benzyloxycarbonyl-L-aspartic acid α-p-nitrophenyl β-benzyl diester by the procedure of Example 1 results in benzyl 3-benzyloxycarbonylamino-N-(DL-1′-methyl-3′-phenyl-n-propyl)-L-succinamate, which, after recrystallization from ether-pentane, melts at about 97°–115° C. and exhibits an optical rotation, in methanol, of −5.5°.

EXAMPLE 14

The reaction of 6.95 parts of 4-fluorophenethylamine with 23.9 parts of N-benzyloxycarbonyl-L-aspartic acid α-p-nitrophenyl, β-benzyl diester by the procedure described in Example 1 results in benzyl 3-benzyloxycarbonylamino-N-4′-fluorophenethyl-L-succinamate, which, after recrystallization from toluene, melts at about 106°–108° C. and exhibits an optical rotation, in methanol, of −9°.

EXAMPLE 15

When an equivalent quantity of 1,1-dimethylphenethylamine is substituted in the procedure of Example 1, there is obtained an oily product, which is extracted with ether. The ether extract is stripped of solvent to afford, as an oil, benzyl 3-benzyloxycarbonylamino-N-1′,1′-dimethylphenethyl-L-succinamate, exhibiting an optical rotation of −6°, in methanol.

EXAMPLE 16

A mixture containing 4.9 parts of benzyl 3-benzyloxycarbonylamino-N-DL-1′-methyl-2′-hydroxyphenethyl-L-succinamate, 0.5 part of palladium black and 120 parts of methanol is shaken with hydrogen at room temperature and approximately 4 atmospheres pressure until 2 molecular equivalents of hydrogen have been absorbed. The catalyst is then removed by filtration and the methanol distilled under reduced pressure to afford the residual crude product. Purification of that material by trituration with ether yields pure 3-amino-N-DL-1'-methyl-2'-hydroxyphenethyl-L-succinamic acid, melting at about 188°–190° C. This compound exhibits an optical rotation, in water, of +10°.

EXAMPLE 17

When an equivalent quantity of benzyl 3-benzyloxycarbonylamino-N-DL-1'-methyl-4''-hydroxyphenethyl-L-succinamate is substituted in the procedure of Example 16, there is obtained 3-amino-N-DL-1'-methyl-4''-hydroxyphenethyl-L-succinamic acid, which softens at about 160° C. and exhibits an optical rotation, in water, of +5°. This compound is represented by the following structural formula.

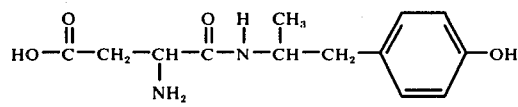

EXAMPLE 18

The substitution of an equivalent quantity of benzyl 3-benzyloxycarbonylamino-N-DL-1'-methyl-4''-fluorophenethyl-L-succinamate in the procedure of Example 16 results in 3-amino-N-DL-1'-methyl-4''-fluorophenethyl-L-succinamic acid, which, after recrystallization from water, melts at about 202.5°–204.5° C.

EXAMPLE 19

By substituting an equivalent quantity of benzyl 3-benzyloxycarbonylamino-N-DL-1'-methyl-3'',4''-dichlorophenethyl-L-succinamate and otherwise proceeding according to the processes of Example 16, there is produced 3-amino-N-DL-1'-methyl-3'',4''-dichlorophenethyl-L-succinamic acid.

EXAMPLE 20

The substitution of an equivalent quantity of benzyl 3-benzyloxycarbonylamino-N-DL-1'-methyl-4''-chlorophenethyl-L-succinamate in the procedure of Example 16, results in 3-amino-N-DL-1'-methyl-4''-chlorophenethyl-L-succinamic acid.

EXAMPLE 21

The hydrogenolysis of an equivalent quantity of benzyl 3-benzyloxycarbonylamino-N-D-1'-methylphenethyl-L-succinamate in 75% acetic acid by the procedure described in Example 16 results in 3-amino-N-D-1'-methylphenethyl-L-succinamic acid, which, after recrystallization from aqueous ethanol, melts at about 222°–225° C. with decomposition and exhibits an optical rotation, in water, of +14°.

EXAMPLE 22

When an equivalent quantity of benzyl 3-benzyloxycarbonylamino-N-L-1'-methylphenethyl-L-succinamate is hydrogenolyzed in 75% acetic acid by the procedure described in Example 16, there is obtained 3-amino-N-L-1'-methylphenethyl-L-succinamic acid, which, after recrystallization from water, melts at about 197°–198° C. with decomposition and displays an optical rotation, in methanol, of −12°.

EXAMPLE 23

When an equivalent quantity of benzyl 3-benzyloxycarbonylamino-N-DL-1'-ethylphenethyl-L-succinamate is hydrogenolyzed in 75% acetic acid by the procedure described in Example 16, there is produced 3-amino-N-DL-1'-ethylphenethyl-L-succinamic acid, which, after recrystallization from methanol-ether, melts at about 158°–163° C. with decomposition and exhibits an optical rotation, in methanol, of +7.8°.

EXAMPLE 24

When an equivalent quantity of benzyl 3-benzyloxycarbonylamino-N-4'-hydroxyphenethyl-L-succinamate is hydrogenolyzed in 75% acetic acid by the procedure described in Example 16, there is produced 3-amino-N-4'-hydroxyphenethyl-L-succinamic acid, which, after recrystallization from water, melts at about 209°–210° C. with decomposition and exhibits an optical rotation, in water, of −21°.

EXAMPLE 25

When an equivalent quantity of benzyl 3-benzyloxycarbonylamino-N-DL-2'-methylphenethyl-L-succinamate is substituted in the procedure of Example 16, there is produced 3-amino-N-DL-2'-methylphenethyl-L-succinamic acid, which, after recrystallization from water, melts at about 182°–188° C. with decomposition and displays an optical rotation, in water, of −15°.

EXAMPLE 26

When an equivalent quantity of benzyl 3-benzyloxycarbonylamino-N-4'-methoxyphenethyl-L-succinamate is substituted in the procedure of Example 16, there is obtained 3-amino-N-4'-methoxyphenethyl-L-succinamate acid, which, after recrystallization from aqueous methanol, melts at about 211°–213° C. with recrystallization and exhibits an optical rotation, in 1 N hydrochloric acid, of −36°.

EXAMPLE 27

The substitution of an equivalent quantity of benzyl 3-benzyloxycarbonylamino-N-(DL-1'-methyl-3'-phenyl-n-propyl)-L-succinamate in the procedure of Example 16 results in 3-amino-N-(DL-1'-methyl-3'-phenyl-n-propyl)-L-succinamate acid, which, after recrystallization from aqueous methanol, melts at about 190°–196° C. with decomposition and exhibits an optical rotation, in 0.1 N hydrochloric acid, of +15.5°.

EXAMPLE 28

The substitution of an equivalent quantity of benzyl 3-benzyloxycarbonylamino-N-4'-fluorophenethyl-L-succinamate in the procedure of Example 16 results in 3-amino-N-4'-fluorophenethyl-L-succinamic acid, which, after recrystallization from water, melts at about 208°–209° C. with decomposition and exhibits an optical rotation, in methanol, of −6°.

EXAMPLE 29

The substitution of an equivalent quantity of benzyl 3-benzyloxycarbonylamino-N-1',1'-dimethylphenethyl-L-succinamate in the procedure of Example 16 affords 3-amino-N-1',1'-dimethylphenethyl-L-succinamic acid, which, after recrystallization from water, melts at about 159°–161° C. and exhibits an optical rotation of −15.5° in methanol.

What is claimed is:

1. A compound of the formula

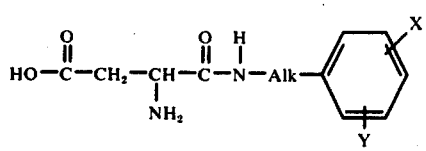

wherein Alk is an alkylene radical containing 2 carbon atoms; X is selected from the group consisting of halogen, hydroxy and methoxy; and Y is selected from the group consisting of hydrogen, halogen and methoxy.

2. The compound according to claim 1 which is 3-amino-N-4′-fluorophenethyl-L-succinamic acid.

3. The compound according to claim 1 which is 3-amino-N-4′-hydroxyphenethyl-L-succinamic acid.

4. The compound according to claim 1 which is 3-amino-N-4′-methoxyphenethyl-L-succinamic acid.

5. A compound of the formula

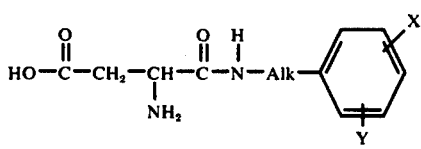

wherein Alk is an alkylene radical containing 3 carbon atoms, and X and Y are selected from the group consisting of hydrogen, halogen, hydroxy and methoxy.

6. The compound according to claim 5 which is 3-amino-N-DL-1′-methyl-4″-fluorophenethyl-L-succinamic acid.

7. The compound according to claim 5 which is 3-amino-N-L-1′-methylphenethyl-L-succinamic acid.

8. The compound according to claim 5 which is 3-amino-N-DL-1′-methyl-4″-hydroxyphenethyl-L-succinamic acid.

9. The compound according to claim 5 which is 3-amino-N-DL-1′-methyl-3″,4″-dichlorophenethyl-L-succinamic acid.

10. A compound of the formula

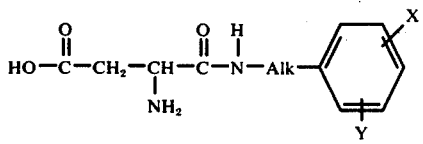

wherein Alk is an alkylene radical containing 4 carbon atoms, and X and Y are selected from the group consisting of hydrogen, halogen, hydroxy and methoxy.

11. The compound according to claim 10 which is 3-amino-N-DL-1′-ethylphenethyl-L-succinamic acid.

12. The compound according to claim 10 which is 3-amino-N-(DL-1′-methyl-3′-phenyl-n-propyl)-L-succinamic acid.

13. The compound according to claim 10 which is 3-amino-N-1′,1′-dimethylphenethyl-L-succinamic acid.

* * * * *